US00PP26979P3

(12) United States Plant Patent
Chiha

(10) Patent No.: US PP26,979 P3
(45) Date of Patent: Jul. 26, 2016

(54) ***GARDENIA AUGUSTA* PLANT NAMED 'KEN04'**

(50) Latin Name: *Gardenia augusta*
Varietal Denomination: KEN04

(71) Applicant: Halim Adib Chiha, Kenthurst (AU)

(72) Inventor: Halim Adib Chiha, Kenthurst (AU)

( * ) Notice: Subject to any disclaimer, the term of this patent is extended or adjusted under 35 U.S.C. 154(b) by 154 days.

(21) Appl. No.: 14/120,721

(22) Filed: Jun. 19, 2014

(65) Prior Publication Data

US 2015/0373888 P1 Dec. 24, 2015

(51) Int. Cl.
*A01H 5/02* (2006.01)

(52) U.S. Cl.
USPC ..... Plt./255

(58) Field of Classification Search
USPC ..... Plt./255
See application file for complete search history.

*Primary Examiner* — Keith Robinson
(74) *Attorney, Agent, or Firm* — Samuel R. McCoy, Jr.

(57) ABSTRACT

'KEN04' is a distinctive variety of *Gardenia augusta* which is characterized by a dense growth habit, fine foliage and a high degree of flowering.

2 Drawing Sheets

Latin name of the genus and species: The Latin name of the genus and species of the novel variety disclosed herein is *Gardenia augusta.*

Variety denomination: The inventive variety of *Gardenia augusta* disclosed herein has been given the variety denomination 'KEN04'.

BACKGROUND OF THE INVENTION

The present invention relates to a new and distinct perennial variety of *Gardenia augusta*, which has been given the variety denomination of 'KEN04'. Its market class is PLT/255. 'KEN04' is a woody ornamental whose intended use is for landscaping and as a decorative plant in ornamental containers.

Parentage: The *Gardenia augusta* variety 'KEN04' was discovered at a wholesale nursery in Kenthurst, New South Wales, Australia, as a spontaneous mutation in a production stock of *Gardenia augusta* 'Radicans' (unpatented). In February of 2004, during routine maintenance work at said nursery, an instant mutation was observed in production stock of *Gardenia augusta* 'Radicans' which possessed finer foliage and a denser growth habit. The instant variety was isolated for further observation where it was evaluated for several months to assess the stability of the distinguishing characteristics. It was noted during development that the instant variety also produced more flowers than the parent.

Asexual Reproduction: 'KEN04' was first propagated asexually by vegetative cuttings at a wholesale nursery in Kenthurst, New South Wales, Australia in 2004 and has since been asexually propagated through ten successive generations. The distinctive characteristics of the inventive 'KEN04' variety are stable from generation to generation; clones of the variety produced by asexual reproduction maintain the distinguishing characteristics of the original plant.

SUMMARY OF THE INVENTION

'KEN04' is a distinctive variety of *Gardenia augusta* which is characterized by a dense growth habit, fine foliage and a high degree of flowering.

BOTANICAL DESCRIPTION OF THE PLANT

Figure 1:
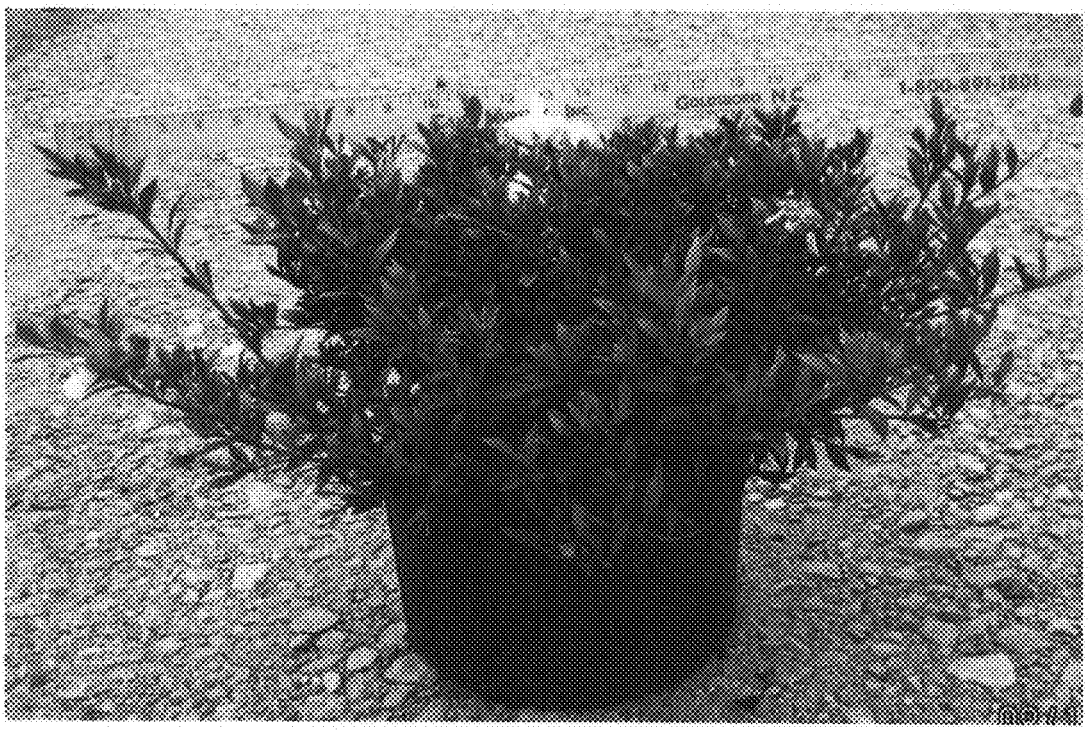
FIG. 1 illustrates an exemplary mature 'KEN04' plant in a 25 cm pot, at approximately one year in age.
Figure 2:
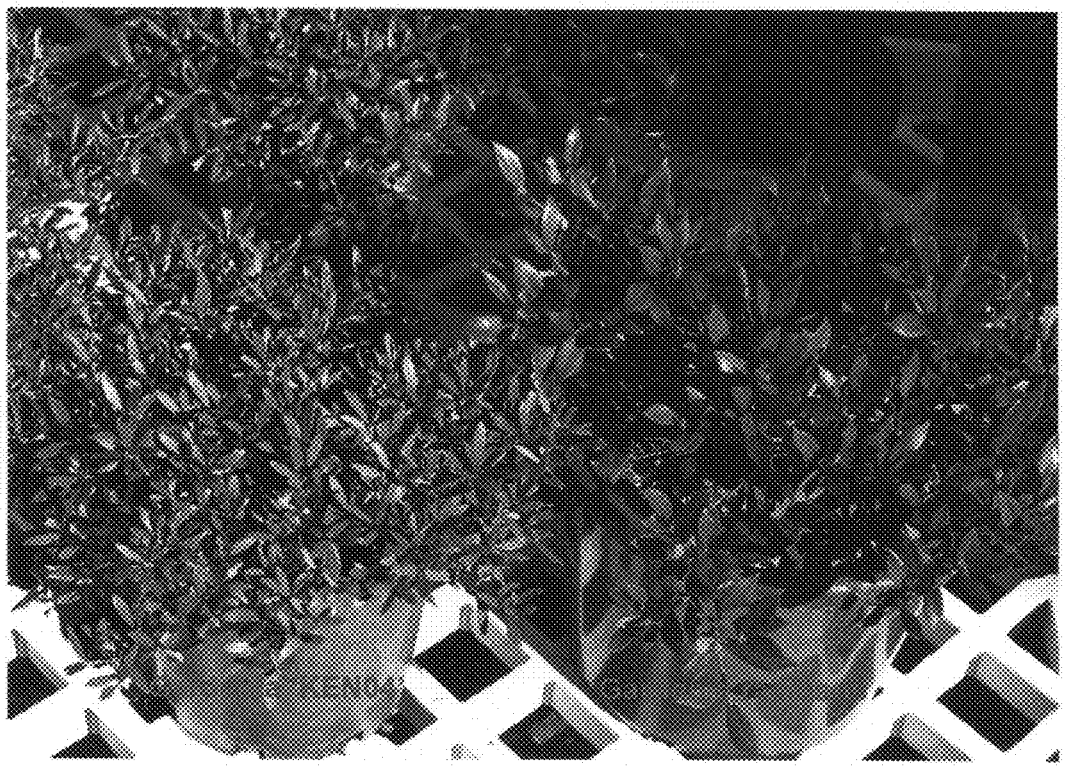
FIG. 2 illustrates a comparison of 'KEN04' (on left) with 'Radicans'; both plants are approximately one year in age. Of note is the fine foliage texture and dense growth habit of 'KEN04'

The following is a detailed botanical description of a new and distinct variety of a *Gardenia augusta* ornamental plant known as 'KEN04'. Plant observations were made on plants grown at a wholesale nursery in Richmond, New South Wales, Australia. Unless indicated otherwise, the descriptions disclosed herein are based upon observations made from 1 year-old 'KEN04' plants grown from rooted cuttings from May 2013 to April 2013 in 25 cm nursery pots filled with soilless potting media, maintained with granular slow release fertilizer and regularly watered with overhead irrigation. No pest and disease measures were taken.

Those skilled in the art will appreciate that certain characteristics will vary with older or, conversely, younger plants. 'KEN04' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on The Royal Horticultural Society Colour Chart, The Royal Horticultural Society, London, 2001 edition. Note that generic color descriptions such as 'green' do not exist in the RHS charts and the corresponding RHS colors are quoted.

'KEN04' is a perennial *Gardenia augusta* plant which is a spontaneous mutation of *Gardenia augusta*. After its selection, 'KEN04' was asexually propagated by division. 'KEN04' has a dense growth habit, fine foliage and a high degree of flowering.

These features and other characteristics are apparent from the description provided below.

Growth Habit, Dimensions and Color

Plant description:

*Plant habit*.—Perennial shrub; mounded to spreading, compact, and dense.

*Height*.—30 cm at maturity.

*Width*.—60 cm at maturity.

*Growth rate*.—Medium vigor.

*Bloom period*.—Summer to autumn in Richmond, New South Wales, Australia.

*Hardiness*.—USDA Zone 7b to 11.

*Environmental tolerances*.—Drought tolerant once established.

*Pest and disease susceptibility or resistance*.—With the exception of a minor occurrence of cottony cushion scale (*Icerya purchase*), common root rot diseases and piercing-sucking insect pests of *Gardenia augusta* have not been observed.

*Propagation*.—Propagation is accomplished using softwood cuttings and plants root well without the use of a rooting compound or hormone. Time to initiate root development is approximately 6 to 8 weeks. An average crop time is approximately 9 months to produce a mature and marketable 15-centimeter container, beginning with a rooted cutting.

Roots: Fibrous and freely branched.

Stems:

*Branching and habit*.—Many freely branched stems arising from a very short central trunk; branch attitude is semi-prostrate to upright.

*Stem dimensions*.—At 10 nodes below active growing point, stems measured at 12 cm in length with a diameter of 3 mm near the base.

*Stem internode length*.—Ranges from 2 to 4 cm.

*Stem strength*.—Weak to medium rigidity.

*Stem shape*.—Round.

*Immature stem color*.—Yellow-green 144B.

*Mature stem color*.—Closest to grey-brown 199B.

*Stem texture*.—Finely pubescent.

Foliage:

*Type*.—Evergreen.

*Division*.—Simple.

*Arrangement*.—Opposite.

*Attachment*.—Sessile.

*Shape*.—Lanceolate, narrow.

*Apex*.—Rounded.

*Base*.—Cuneate.

*Venation*.—Pinnate to reticulate.

*Vein color* (*adaxial surfaces*).—Midrib is yellow-green 144A.

*Vein color* (*abaxial surfaces*).—Yellow-green 146B.

*Margins*.—Entire.

*Texture* (*adaxial surface*).—Very smooth and glabrous.

*Texture* (*abaxial surface*).—Smooth and glabrous.

*Mature leaf dimensions*.—Approximate length 35 mm, width 9 mm.

*Leaf color* (*adaxial surface*).—Yellow-green 147A.

*Leaf color* (*abaxial surface*).—Yellow-green 144A.

Inflorescence:

*Type*.—Flowers are solitary.

Flowers:

*Bud*.—Shape is oblong; apex is rounded; dimensions are approximately 30 to 40 mm long and 15 to 20 mm wide at 2 to 4 days prior to bud-break. Color is yellow-green 144B.

*Floral type*.—Perfect; double; incomplete or near-incomplete.

*Corolla*.—Salverform flowers with outer corolla of 6 true petals fused at the base and numerous petaloids held tightly and standing erect; outer corolla is approximately perpendicular to a floral tube; over all dimensions are approximately 45 to 60 mm across the outer corolla and 45 to 60 mm deep, from base of floral tube to the apex of erect-standing petaloids. Sweet fragrance.

*Petals*.—Six; Margin: entire and slightly wavy; Texture: glabrous on both surfaces.

*Petal color* (*at anthesis*).—White 155C, fading to yellow 10D.

*Floral tube length*.—12 mm long.

*Floral tube width*.—3 mm wide at the proximal end, and 5 mm wide at the distal end.

*Dimensions of the unfused portion of the petal*.—25 mm long and 11 mm wide, at the widest point.

*Shape of unfused portion of the petal*.—Obovate; apex is acute; base is connate.

*Petaloids*.—Attitude is erect, standing nearly perpendicular to the flat-laying petals. Color is 155C at anthesis, fading to yellow 10D. Dimensions vary, but petaloids become increasing smaller near the center.

*Calyx*.—Synsepalous; tubular in shape with 5 or 6 subulate sepal lobes with acute apices and entire margins. Length overall, including sepal lobes, is approximately 35 mm; sepal lobe dimensions are approximately 10 mm long and 3 mm wide. Color is yellow-green 144B. Texture of both the upper and lower surfaces is glabrous.

*Peduncle*.—Approximately 5 to 12 mm long and 2.5 mm in diameter. Color is yellow-green 144B. Peduncles are smooth and glabrous. Strength is weak.

Reproductive organs: Typically, the stamens are reduced to irregular staminoids which are approximately 12 mm long; the color is 155C at anthesis, fading to yellow 10D; approximate quantity of staminoids is six. The single pistil is approximately 20 mm long and 1 mm in diameter; the style length is approximately 18 mm long and the color is green-white 157A; the obovate stigma is approximately 2 mm in diameter; stigma color is 154D.

Fruit and seed production: No fruit and seed production observed due to the incomplete flowers.

Comparison of KEN04 With the Parent and Closest Known Variety of *Gardenia augusta*

By comparison with the parent, which is also the closest known variety, 'KEN04' has a more compact growth habit, a more narrow leaf width and more flowers per plant.

'KEN04' has shorter stem internodes which translates to a higher leaf count on each branch and an overall denser growth habit. Internodes of 'KEN04' are approximately 25% shorter than those of 'Radicans'. The shortened internode length also translates to more floral buds per lateral branch when compared to the parent.

'KEN04' has a finer foliage texture compared to 'Radicans'. Mature leaves of 'KEN04' are 35 mm long by 9 mm wide for a length-to-width ratio of 3.89, whereas the length-to-width ratio of 'Radicans' is 2.00 with approximate dimensions of 40 to 50 mm long and 20 to 25 mm wide.

The combination of its dense growth habit, fine foliage and a high degree of flowering makes 'KEN04' a desirable ornamental plant suited for mass production for pot and landscape use.

That which is claimed is:

1. A new and distinct variety of *Gardenia augusta* plant named 'KEN04', substantially as described and illustrated herein.

* * * * *